United States Patent
Kumar et al.

(10) Patent No.: US 11,690,805 B2
(45) Date of Patent: Jul. 4, 2023

(54) MULTI-PARTICULATE PHARMACEUTICAL COMPOSITION OF QUETIAPINE

(71) Applicant: Sun Pharmaceutical Industries Limited, Maharashtra (IN)

(72) Inventors: Amit Kumar, Bihar (IN); Ravindra Agarwal, Rajasthan (IN); Pulak Kumar Metia, West Bengal (IN); Kalaiselvan Ramaraju, Tamil Nadu (IN); Sumit Madan, New Delhi (IN); Romi Barat Singh, Uttar Pradesh (IN)

(73) Assignee: Sun Pharmaceutical Industries Limited, Mumbai (IN)

( * ) Notice: Subject to any disclaimer, the term of this patent is extended or adjusted under 35 U.S.C. 154(b) by 0 days.

(21) Appl. No.: 17/550,785

(22) Filed: Dec. 14, 2021

(65) Prior Publication Data

US 2022/0105040 A1   Apr. 7, 2022

Related U.S. Application Data

(63) Continuation of application No. PCT/IB2021/058588, filed on Sep. 21, 2021.

(30) Foreign Application Priority Data

Sep. 21, 2020  (IN) .............................. 202021040886

(51) Int. Cl.
*A61K 9/16* (2006.01)
*A61K 31/554* (2006.01)
*A61K 47/32* (2006.01)
*A61K 47/38* (2006.01)

(52) U.S. Cl.
CPC .......... *A61K 9/1676* (2013.01); *A61K 9/1682* (2013.01); *A61K 31/554* (2013.01); *A61K 47/32* (2013.01); *A61K 47/38* (2013.01)

(58) Field of Classification Search
None
See application file for complete search history.

(56) References Cited

U.S. PATENT DOCUMENTS

| 10,709,668 B2 * | 7/2020 | Johns ................... A61K 9/4808 |
| 2005/0158383 A1 | 7/2005 | Boehm et al. |
| 2009/0220593 A1 | 9/2009 | Gulati et al. |

OTHER PUBLICATIONS

Siepmann et al. (Polymer blends for controlled release coatings, Journal of Controlled Release 125 (2008) 1-15). (Year: 2008).*
Ong et al. (Effects of Hypromellose as a pore former in aqueous ethyl cellulose dispersion: Characterization of Dispersion Properties, Controlled Release Society, Poster Reprint, Jul. 2006). (Year: 2006).*
Engels et al. (The innovative Use of micronized Hydroxypropyl methylcellulose as a pore former in dry coatings of ethyl cellulose barrier membrane coatings on multi-particulates; Nov. 2016). (Year: 2016).*
Siepman et al. (Polymer blends for controlled release coatings, Journal of Controlled Release 125 (2008) 1-15). (Year: 2008).*
International Search Report issued in PCT/IB2021/058588, dated Dec. 17, 2021.
Written Opinion of the International Searching Authority, Issued in PCT/IB2021/058588, dated Dec. 17, 2021.

* cited by examiner

*Primary Examiner* — Melissa S Mercier
(74) *Attorney, Agent, or Firm* — Sughrue Mion, PLLC

(57) ABSTRACT

The present invention discloses an extended release multi-particulate sprinkle composition comprising a plurality of discrete units, each discrete unit comprising quetiapine or a pharmaceutically acceptable salt thereof and one or more pharmaceutically acceptable excipients.

20 Claims, No Drawings

MULTI-PARTICULATE PHARMACEUTICAL COMPOSITION OF QUETIAPINE

CROSS-REFERENCE TO RELATED APPLICATIONS

This application is a Continuation of International Application No. PCT/IB2021/058588, filed on Sep. 21, 2021, which is based on and claims priority to Indian Patent Application No. 202021040886 filed on Sep. 21, 2020, the disclosures of which are incorporated by reference herein in their entireties.

FIELD OF THE INVENTION

The present invention relates to an extended release multi-particulate sprinkle composition comprising a plurality of discrete units, each discrete unit comprising quetiapine or a pharmaceutically acceptable salt thereof and one or more pharmaceutically acceptable excipients, wherein said multi-particulate composition is sprinkled onto soft foods or edible material or liquids for oral administration.

BACKGROUND OF THE INVENTION

Quetiapine is a psychotropic agent belonging to a chemical class, the dibenzothiazepine derivatives. The chemical name of quetiapine is 2-[2-(4-dibenzo[b,f][1,4]thiazepin-11-yl-1-piperazinyl)ethoxy]-ethanol. In general, it is present in various oral formulations like tablets and capsules in its salt forms, preferably as the fumarate salt. The molecular formula for its fumarate salt is $C_{42}H_{50}N_6O_4S_2 \cdot C_4H_4O_4$ and it has a molecular weight of 883.11. The structural formulae of quetiapine and quetiapine fumarate are shown in below Formula I and II, respectively:

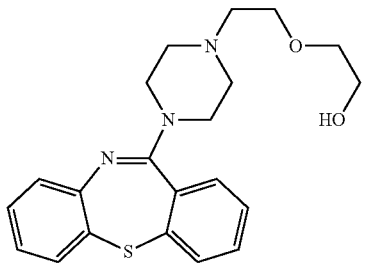
Formula-I

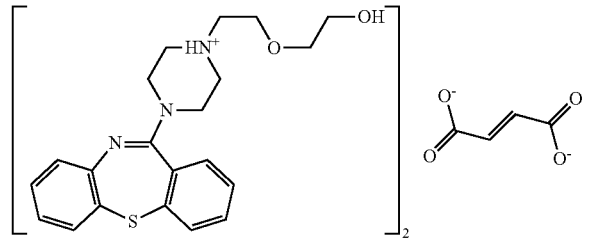
Formula-II

Quetiapine fumarate is a white to off-white crystalline powder which is moderately soluble in water.

Quetiapine was initially approved by the FDA in 1997, it is a second-generation atypical antipsychotic used in schizophrenia, major depression, and bipolar disorder. Quetiapine demonstrates a high level of therapeutic efficacy and low risk of adverse effects during long-term treatment. Quetiapine is used in the symptomatic treatment of schizophrenia, in management of acute manic or mixed episodes in patients with bipolar I disorder, as a monotherapy or combined with other drugs.

Various solid oral dosage forms of quetiapine are known. Quetiapine fumarate is commercially available as an extended release tablet formulation and is marketed under the brand name SEROQUEL XR®.

U.S. Pat. No. 5,948,437 covers the marketed product and discloses a sustained release quetiapine tablet formulation wherein the drug is compressed with a gelling agent to form the tablet.

The commercially available extended release tablet of quetiapine fumarate is used for treatment of schizophrenia, acute treatment of manic or mixed episodes associated with bipolar disorder, in treatment of depressive episodes of bipolar disorders and as an adjunctive treatment of major depressive disorder.

Solid oral dosage forms are not suitable for patients having difficulty swallowing or with dysphagia as in case of geriatric and pediatric patients. Further, conventional solid oral dosage forms like tablets and capsules are intended to be swallowed as whole. The available marketed formulation of quetiapine should not be crushed or chewed, as drug release will be compromised. The dosage and administration section of the SEROQUEL XR® prescribing information states, "SEROQUEL XR® tablets should be swallowed whole and not split, chewed or crushed." It is also mandatory as per the SEROQUEL XR® label that the patient should take the tablet without food or with light food. Therefore, there is poor compliance for the marketed formulation in patients having dysphagia or with difficulty swallowing.

Dosing regimens for various antipsychotic solid oral dosage forms generally include two or three tablets/capsules per day, however, such regimens were found to be associated with problems such as lack of convenience, and more importantly lack of compliance, particularly in patients with dysphagia and swallowing difficulty. Dysphagia plays a critical role in medication management, since many older adults cannot swallow whole tablets and capsules because of swallowing difficulty. Dysphagia can be caused by difficulties overriding the natural instinct to chew solids/foodstuff before swallowing, or it may be a more complex disorder of swallowing function affecting the ability to manage all food and fluid intake. The marketed formulation SEROQUEL XR® (U.S. Pat. No. 5,948,437) has not been very helpful in such patients. Further, because the control of quetiapine plasma levels is critical during treatment, failures or incidents, such as, the one that can be seen with patients having swallowing difficulty, leads to instances of non-compliance or missed dosing, which can be detrimental to patient health and safety.

Thus, there exists a need for a dosage form or composition of quetiapine which provides a better compliance for the patients having dysphagia or difficulty swallowing or related conditions like where s patient is hesitant or not willing to take medicine.

SUMMARY OF THE INVENTION

The present invention provides an extended release multi-particulate composition comprising a plurality of discrete units, each discrete unit comprising quetiapine or a pharmaceutically acceptable salt thereof and one or more pharmaceutically acceptable excipients, whereby the composition can also be sprinkled onto soft foods or edible material or liquids for oral administration.

In another aspect, the present invention provides a stable dosage form, wherein the release profile of the quetiapine or its pharmaceutically acceptable salt is not affected by sprinkling the multi-particulate composition according to the present invention onto soft foods or edible material or liquids for oral administration. The integrity of the coating is not influenced by longer exposure to soft foods or edible material or liquids. The dosage form may be taken with or without food.

In some aspects, the multi-particulate composition can be administered through a feeding tube in a long-term care setting to critically ill patients by dispersing in an aqueous media before administration.

In one aspect, the present invention provides discrete units comprising quetiapine, wherein the discrete units may be in the form of a pellet, granule, spheroid, particle, mini-tablet or bead.

In another aspect, the multi-particulate sprinkle dosage form is substantially free of food effect and devoid of problems associated with other known marketed formulations such as delay in gastric emptying due to larger size of tablets or capsules and variability in bioavailability.

In some aspects, the present invention provides an extended release multi-particulate sprinkle dosage form comprising a plurality of discrete units, wherein each unit comprises a drug core comprising quetiapine or a pharmaceutically acceptable salt thereof; at least two coatings on the drug core wherein one of the at least two coatings comprises a pH sensitive polymer; and wherein the release of the drug is controlled by a combination of the said at least two coatings.

In one aspect, each of the discrete units according to the present invention comprises at least two coatings on the drug core to control the release of the drug from the core; wherein at least one coating comprises a pH sensitive polymer.

In another aspect, each of the discrete units according to the present invention comprises at least two coatings on the drug core for controlling the release of the drug, wherein one of the at least two coatings comprises a pH neutral polymer, and the other coating is a pH sensitive polymer.

In yet another aspect, the core of the discrete units comprises an active ingredient quetiapine or its pharmaceutically acceptable salt, and the coating is devoid of any active ingredient.

In a further aspect according to the present invention, the core is devoid of a release-controlling polymer.

In one aspect, the extended release multi-particulate sprinkle dosage form according to the present invention comprises a drug core of quetiapine or a pharmaceutically acceptable salt thereof, coated with a pH neutral polymer coating and a pH sensitive polymer coating, wherein the drug release from the dosage form is controlled by a combined effect of the pH neutral polymer coating and the pH sensitive polymer coating.

DESCRIPTION OF THE INVENTION

As used herein, the word "a" or "plurality" before a noun represents one or more of the particular noun.

For the terms "for example" and "such as," and grammatical equivalences thereof, the phrase "and without limitation" is understood to follow unless explicitly stated otherwise. As used herein, the term "about" is meant to account for variations due to experimental error. All measurements reported herein are understood to be modified by the term "about," whether or not the term is explicitly used, unless explicitly stated otherwise.

The term "dosage form" as used herein the description, can be used interchangeably with the term 'composition' or 'formulation' or 'pharmaceutical preparation'.

The term "coating" as used herein the description, can be used interchangeably with the term "coat" or "layer" around the core.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, and other references mentioned herein are incorporated by reference in their entirety. In case of conflict, the present specification, including definitions, will control.

The present inventors have developed a stable sprinkle dosage form of quetiapine in the form of a multi-particulate dosage form comprising a plurality of discrete units. Such dosage form is believed to be bioequivalent to the marketed SEROQUEL XR® formulation and can be easily administered by sprinkling on the food. Further, such dosage form when administered as a sprinkle over soft food or edible material or liquid for oral administration, it becomes easier for patients to comply as well as get the maximum benefit out of therapy.

The present invention relates to an extended release multi-particulate composition comprising a plurality of discrete units, each discrete unit comprising quetiapine or a pharmaceutically acceptable salt thereof and one or more pharmaceutically acceptable excipients, which is sprinkled onto soft foods or edible material or liquids for oral administration.

In another embodiment, the present invention provides a stable dosage form, wherein the release profile of the quetiapine or its pharmaceutically acceptable salt is not affected by sprinkling the multi-particulate composition according to the present invention onto soft foods or edible material or liquids for oral administration. The integrity of the coating is not influenced by longer exposure to soft foods or edible material or liquids. The said dosage form may be taken with or without food.

In a further embodiment, the multi-particulate composition can be administered through a feeding tube in a long-term care setting to critically ill patients by dispersing in an aqueous media before administration.

According to one embodiment of the present invention, the discrete units may be in the form of a pellet, granule, spheroid, particle, mini-tablet or bead.

In another embodiment, the multi-particulate sprinkle dosage form according to the present invention is bioequivalent to the marketed quetiapine formulation available under the brand name SEROQUEL XR®. Further, the dosage form is substantially free of food effect and devoid of problems associated with other known marketed formulations such as delay in gastric emptying due to a larger size of tablets or capsules and variability in bioavailability.

In one embodiment, the present invention provides an extended release multi-particulate sprinkle dosage form comprising a plurality of discrete units, wherein each unit comprises a drug core comprising quetiapine or a pharmaceutically acceptable salt thereof; at least two coatings on the drug core wherein one of the at least two coatings comprises a pH sensitive polymer; and wherein the release of the drug is controlled by a combination of said at least two coatings.

In another embodiment, the present invention provides an extended release multi-particulate sprinkle dosage form comprising a plurality of discrete units, wherein each unit comprises a drug core comprising quetiapine or a pharmaceutically acceptable salt thereof; at least two coatings on the drug core to control the release of the drug from the core; wherein at least one coating comprises a pH sensitive polymer.

In yet another embodiment, the extended release multi-particulate sprinkle dosage form according to the present invention comprises a plurality of discrete units, wherein each unit comprises a drug core comprising quetiapine or a pharmaceutically acceptable salt thereof; at least two coatings on drug core controlling the release of drug, wherein one of the at least two coatings comprises a pH neutral polymer, and the other coating is a pH sensitive polymer.

In another embodiment, the discrete units according to present invention comprise a core and at least two coatings. In another embodiment, the discrete units comprise a core and more than one coating for modified release of the drug from the core.

In another embodiment, the core of the discrete units comprises an active ingredient quetiapine or its pharmaceutically acceptable salt, and the coating is devoid of any active ingredient.

In one aspect of the present invention, the coating may optionally comprise one or more active ingredients.

In another embodiment of the present invention, the core is devoid of a release-controlling polymer.

In one embodiment, the multi-particulate sprinkle composition of the invention may be modulated to provide an extended drug release, controlled drug release, sustained drug release, prolonged drug release, delayed drug release, modified drug release, immediate drug release or a combination of immediate and extended drug release.

The term "granules", "pellets" or "spheroids" as used herein can be used interchangeably, and includes agglomeration from apparent solid powder particles to large multi-particulates. The agglomeration may be achieved by either granulation, compaction, extrusion, slugging, drug loading or the like. Such granules, pellets or spheroids have good flow property and these may be spherical or oval in shape, and may have a density higher than a powder. The granules or pellets or spheroids are coated, in particular, they can be preferably coated with at least one functional coating, as described herein. The average diameter of coated pellets or granules is about 500 µm to about 1800 µm, or about 600 µm to about 1500 µm. Also included are granules as defined in USP <1151>, which is incorporated herein by reference.

The term "functional coating" in the context of this disclosure refers to one or more controlled release layers, particularly an extended release layer that surrounds a drug core. The term "extended release" as used herein can be used interchangeably with term "controlled release", "modified release" or "sustained release" and refers to a means of releasing an active agent from the dosage form thereof such that it is available to the site of absorption by the body over a period of time.

The terms "non-functional coating" or "non-functional film coat" in the context of the present disclosure refers to a coating that does not materially affect the release of quetiapine or a pharmaceutically acceptable salt thereof from the formulation or dosage form. A non-functional coating or non-functional film coat may still include some functions not related to the dissolution of quetiapine, such as taste, color, or physical integrity.

The term "sprinkle" as used herein means that the multi-particulate pharmaceutical composition is to be added onto food or any edible material, or liquid, such as water, juices etc., before administration. The pellets or granules or spheroids or particle of the multi-particulate pharmaceutical composition may be packed in sachet or pouch or filled into capsules and may be sprinkled onto soft food or edible material or into a liquid. Alternatively, multi-particulate pharmaceutical composition may also be in the form of a dispersible dosage form which can be dispersed in a liquid to yield a dispersion of the individual particles before drinking. The multi-particulate pharmaceutical composition of the present invention is configured so as to be administered by initially opening a sachet or pouch or capsule filled with it and transferring it to a vehicle, such as a soft food, for example, applesauce, pudding, custard, oatmeal and yoghurt. Then, the vehicle into which the composition is sprinkled is swallowed immediately. The multi-particulate pharmaceutical composition of the present disclosure may be swallowed as a whole when in capsule, and can also be sprinkled onto the vehicle. Alternatively, geriatric patients who have difficulty swallowing may add the composition of the present invention that has been filled into sachet or pouch or capsule, into a liquid medium, such as water, to obtain a suspension. The suspension may be then orally administered through, e.g., a nasogastric tube into the stomach.

The term "mixture" as used herein means that the quetiapine or a pharmaceutically acceptable salt thereof is mixed uniformly with excipients of various categories such as stabilizers, alkalizing agents, buffering agents, disintegrants or diluents.

The term "stable" as used herein, refers to a physico-chemical stability which means that the extended/delayed release coat over the multi-particulate composition retain its structural integrity and does not rupture in a significant way after exposure to acidic or any external environment for the given time period as determined by the drug release and also includes chemically stability which means the multi-particulate composition remains stable when stored:

under the temperature and humidity conditions of 40° C./75% RH for at least 6 months; or under the temperature and humidity conditions of 30° C./65% RH for at least 6 months; or under the temperature and humidity conditions of 25° C./60% RH for at least 6 months.

The term "pharmaceutically acceptable salt" as used herein means a salt which is, within the scope of sound medical judgment, suitable for use in contact with the tissues of humans and lower animals without undue toxicity, irritation, allergic response and the like, commensurate with a reasonable benefit/risk ratio, and effective for their intended use. Representative alkali or alkaline earth metal salts include the sodium, calcium, potassium and magnesium salts, and the like. U.S. Pat. No. 4,879,288 (hereafter '288) discloses a process for the preparation of quetiapine or a pharmaceutically acceptable salt thereof which includes hydrochloride, maleate, fumarate, citrate, phosphonate, methane sulphonate, and hemifumarate salt. The disclosure of '288 also mentions that the compound of formula II (quetiapine) can form a salt with physiologically acceptable organic and inorganic acids like hydrochloride, maleate, fumarate, citrate, phosphonate, methane sulphonate, and hemifumarate salt. Only the hydrochloride, maleate and hemifumarate salts of quetiapine have been prepared, the disclosure of which is incorporated herein by reference.

The term "therapeutically effective amount" as used herein means that amount of quetiapine or its pharmaceutically acceptable salt that when administered to a mammal for treating a disease state, disorder or condition, is sufficient to effect such treatment. The therapeutically effective amount will vary depending on the compound, the disease and its severity and the age, weight, physical condition and responsiveness of the mammal or human to be treated.

The term "bioequivalent" as used herein has its ordinary meaning as understood by those skilled in the art and thus includes, without limitation, a drug or dosage form that, upon administration to a suitable patient population, provides principle pharmacokinetic parameters, e.g., AUC and $C_{max}$ that are in the range of 80% to 125% of those provided by a reference standard. Also the terms "bioequivalent" or "bioequivalence", as used herein are used interchangeably and describes pharmaceutical equivalent products that display comparable bioavailability when studied under similar experimental conditions. This term also used herein is consistent with the definitions and concepts assigned to them under the U.S. Drug Price Competition and Patent Term Restoration Act of 1984, including the conditions set forth in § 5500)(7)(B), and 21 CFR § 320.24, which are incorporated herein by reference in their entirety. Thus, the term "bioequivalent" as used herein, refers to the equivalent release of the same drug substance from two or more drug products or formulations which lead to an equivalent rate and extent of absorption from these products or formulations. In other words, if a drug product contains a drug substance that is chemically identical and is delivered to the site of action at the same rate and extent as another drug product, then it is equivalent. Methods to define bioequivalence can be found in 21 CFR 320.24, and include (1) pharmacokinetic (PK) studies, (2) pharmacodynamic (PD) studies, (3) comparative clinical trials, and (4) in-vitro studies, which are incorporated herein by reference in their entireties. Of course, the choice of study used, such as illustrated herein in the present specification, is based upon the site of action of the drug and the ability of the study design to compare drug delivered to that site by the two products.

By the term, "bioavailability", it refers to the definition and concepts assigned to this term under the Drug Price Competition and Patent Term Restoration Act of 1984, in particular in § 550(j)(8)(B) and is used herein consistent with such definition and concept, which is incorporated herein by reference in its entirety.

According to the present invention, particle size of the coated multi-particulate discrete units (pellets or granules or spheroids) may be such that D10 ranges from about 500 µm to about 1100 µm; D50 ranges from about 950 µm to about 1250 µm and D90 ranges from about 1150 µm to about 1800 µm; Preferably D10 ranges from about 700 µm to about 1000 µm; D50 ranges from about 1050 µm to about 1150 µm and D90 ranges from about 1200 µm to about 1500 µm.

In one embodiment, the strength of the said quetiapine multi-particulate dosage form is 50 mg, 150 mg, 200 mg, 300 mg, or 400 mg. All doses strengths of the composition are expressed as milligrams of quetiapine base, not as quetiapine fumarate salt.

In another embodiment, the multi-particulate dosage form according to the present invention may be administered twice or thrice daily (BID or TID) depending upon the dose requirement. In an aspect for instance, when the required dose is 800 mg, two 400 mg sachets may be administered together, when the required dose is 400 mg, a single sachet may be administered. In another aspect, the dosage form according to present invention can be administered as a sprinkle dosage form over soft food or edible material or liquid for oral administration, thereby a higher dose can be accommodated in a single administration without any swallowing difficulty. In one embodiment, the multi-particulate dosage form according to the present invention may be administered once daily.

In one embodiment, according to the present invention, the discrete unit of the multi-particulate composition comprises a drug core with one or more pharmaceutically acceptable excipients, wherein the core is coated with at least one functional coating.

In another embodiment according to the present invention, the discrete unit of the multi-particulate composition comprises a drug core and optionally one or more non-functional coatings.

In an embodiment of the present invention, the core containing the active ingredient quetiapine or its pharmaceutically acceptable salt is coated by functional coating layers comprising one extended release coating followed by one delayed release coating. In another embodiment of the present invention, the core containing the active ingredient quetiapine or its pharmaceutically acceptable salt is coated by functional coating layers comprising a delayed release coating followed by an extended release coating. In another embodiment of the present invention, the core containing the active ingredient quetiapine or its pharmaceutically acceptable salt is coated by functional coating layers comprising an extended release coating, a delayed release coating or combination thereof. In a related embodiment of the present invention, the core containing the active ingredient quetiapine or its pharmaceutically acceptable salt may also optionally be coated with a non-functional coating.

In a further embodiment, the present invention provides an extended release multi-particulate sprinkle dosage form comprising a plurality of discrete units, wherein each unit comprises: a core comprising quetiapine or a pharmaceutically acceptable salt thereof, at least one coating comprising a pH neutral polymer surrounding the core and at least one coating comprising a pH sensitive polymer surrounding the core, wherein the drug release from the multi-particulate dosage form is controlled by pH sensitive and pH neutral polymers in coatings surrounding the core.

In yet another embodiment, the present invention provides an extended release multi-particulate sprinkle dosage form comprising a plurality of discrete units, wherein each unit comprises a drug core comprising quetiapine or a pharmaceutically acceptable salt thereof; an extended release coating and a delayed release coating surrounding the core.

In another embodiment, the present invention provides a controlled release sprinkle composition comprising a plurality of particulates, wherein each particulate comprises: a core comprising quetiapine, a pH neutral polymer layer surrounding the core and a pH sensitive polymer layer surrounding the core, wherein the average particle size (D50) of coated particulates is from 0.7 to 1.6 mm or average particle size of the coated particulate is less than 1.6 mm.

In an embodiment of the present invention, the multi-particulate dosage form has an extended-release coating which comprises a pH neutral polymer in an amount of about 5% to about 25% based on the weight of drug core.

In one embodiment of the present invention, the multi-particulate dosage form has an extended release coating which comprises a pH neutral polymer in an amount of about 50% to about 80% based on the weight of the extended release coating, preferably about 55% to about 75% based on weight of the extended release coating.

In yet another embodiment of the present invention, the extended release coating comprises about 12% to about 32% w/w of the drug core, preferably about 12% to 20% w/w.

In another embodiment of the present invention, the multi-particulate dosage form has a delayed release coating which comprises a pH sensitive polymer in an amount of about 10% to about 30% based on the weight of drug core.

In one embodiment of the present invention, the multi-particulate dosage form has a delayed release coating which comprises a pH sensitive polymer in an amount of about 55% to about 95% based on the weight of the delayed release coating, preferably about 60% to about 90% based on weight of the delayed release coating.

In a further embodiment of the present invention, the delayed release coating comprise about 15% to about 45% w/w of the drug core, preferably about 15% to about 35% of the drug core.

In one embodiment of the present invention, the active ingredient in the composition comprises about 35% to about 70% w/w of a unit dosage form.

In yet another embodiment of the present invention, the active ingredient in the composition comprises about 50% to about 70% w/w of the core.

In another embodiment, the present invention provides an extended release multi-particulate sprinkle dosage form comprising a plurality of discrete units, wherein each unit comprises a drug core comprising quetiapine or a pharmaceutically acceptable salt thereof; an extended release coating and a delayed release coating surrounding the core, wherein the drug release from the multi-particulate dosage form is controlled with pH neutral and pH sensitive polymers in the coatings respectively. In yet another embodiment, the present invention provides an extended release multi-particulate sprinkle dosage form comprising a plurality of discrete units, wherein each unit comprises a drug core comprising quetiapine or a pharmaceutically acceptable salt thereof, at least two coatings on the drug core to control the release of the drug from the core, wherein each coating comprises a pH sensitive polymer, a pH neutral polymer or a combination thereof.

In one embodiment, the present invention provides an extended release multi-particulate sprinkle dosage form comprising a plurality of discrete units, wherein each unit comprises a drug core comprising quetiapine or a pharmaceutically acceptable salt thereof; an extended release coating comprising a pH neutral polymer and a delayed release coating comprising a pH sensitive polymer surrounding the core, wherein the drug release from the multi-particulate dosage form is controlled with a combination of pH neutral and/or pH sensitive polymers in the coatings.

In yet another embodiment, the present invention provides an extended release multi-particulate sprinkle dosage form comprising a plurality of discrete units, wherein each unit comprises a drug core comprising quetiapine or a pharmaceutically acceptable salt thereof; a delayed release coating comprising a pH sensitive polymer and an extended release coating comprising a pH neutral polymer surrounding the core, wherein the drug release from the multi-particulate dosage form is controlled with a combination of pH sensitive and/or pH neutral polymers in the coatings.

In a related embodiment, the present invention provides a multi-particulate dosage form wherein the extended-release coating or the coating with pH neutral polymer comprises a water-insoluble polymer.

In some embodiments, the extended release multi-particulate sprinkle dosage form according to present invention comprises a plurality of discrete units, wherein each unit comprises: a drug core comprising quetiapine or a pharmaceutically acceptable salt thereof; at least two coatings on drug core for controlling the release of quetiapine from the drug core wherein one of the at least two coatings comprises a pH sensitive polymer; and wherein said dosage form when administered orally as a single dose has a mean Cmax under fasting condition in the range of about 180 ng/mL to about 450 ng/mL and a mean Cmax under fed condition in the range of about 250 ng/mL to about 650 ng/mL.

In some embodiments, the extended release multi-particulate sprinkle dosage form according to present invention comprises a plurality of discrete units, wherein each unit comprises: a drug core comprising quetiapine or a pharmaceutically acceptable salt thereof; at least two coatings on drug core for controlling the release of quetiapine from the drug core wherein one of the at least two coatings comprises a pH sensitive polymer; and wherein said dosage form when administered orally as a single dose has a mean $AUC_{0\text{-}inf}$ under fasting condition is in the range of 4000 hr·ng/mL to 4800 hr·ng/mL and a mean $AUC_{0\text{-}inf}$ under fed condition in the range of about 4300 hr·ng/mL to 6300 hr·ng/mL.

In one embodiment, the extended release multi-particulate sprinkle dosage form according to present invention comprises a plurality of discrete units, wherein each unit comprises: a drug core comprising quetiapine or a pharmaceutically acceptable salt thereof; at least two coatings on drug core for controlling the release of quetiapine from the drug core wherein one of the at least two coatings comprises a pH sensitive polymer, and wherein the said dosage form when administered orally as a single dose with high fat meals results in not more than (NMT) a 35% change in Cmax or AUC when compared to a similar dosing under fasting conditions.

In another embodiment, the present invention provides a pharmaceutical composition of quetiapine or a pharmaceutically acceptable salt thereof, wherein said composition is believed to be bioequivalent to an extended release multi-particulate sprinkle dosage form comprising a plurality of discrete units, wherein each unit comprises: a drug core comprising quetiapine or a pharmaceutically acceptable salt thereof; at least two coatings on drug core for controlling the release of quetiapine from the drug core wherein one of the at least two coatings comprises a pH sensitive polymer; and wherein the said dosage form when administered orally as a single dose with high fat meals results in not more than (NMT) a 35% change in Cmax or AUC when compared to a similar dosing under fasting conditions.

In a further embodiment, the multi-particulate dosage form according to the present invention further comprises a pore former in the extended release coating, wherein the ratio of extended release polymer and pore former in the coating is in a ratio of 70:30 to 99:1 or 75:25 to 97:3 or 80:20 to 95:5. Preferably, the ratio is 80:20 to 95:5. In another embodiment, the multi-particulate dosage form according to the present invention further comprises a pore former in the pH neutral coating, wherein the ratio of pH neutral polymer and pore former in the coating is in a ratio of 70:30 to 99:1 or 75:25 to 97:3 or 80:20 to 95:5. Preferably the ratio is 80:20 to 95:5.

In an embodiment, the extended release multi-particulate sprinkle dosage form comprises a plurality of discrete units, wherein each unit comprises: a drug core comprising quetiapine or a pharmaceutically acceptable salt thereof; at least two coatings on drug core wherein one of the at least two coatings comprises a pH sensitive polymer; and wherein the release of the drug is controlled by a combination of said at least two coatings, wherein the dosage form further comprises a pore former and the ratio of one of the two coatings and the pore former is 80:20 to 95:5.

In one embodiment, the multi-particulate sprinkle dosage form according to the present invention comprises coated particulates having a particle size in range of 0.5 mm-1.6 mm, and said sprinkle dosage form releases not more than 20% of quetiapine after two hours, when measured in a United States Pharmacopeia (USP) type I dissolution apparatus, 200 rpm, at a temperature of 37° C.±0.5° C. in 900 mL of pH 4.80 citrate buffer media.

In a further embodiment, the present invention provides a pharmaceutical composition of quetiapine or a pharmaceutically acceptable salt thereof, wherein said composition is believed to be bioequivalent to an extended release multi-particulate sprinkle dosage form comprising a plurality of discrete units, wherein said multi-particulate sprinkle dosage form comprises coated particulates having a particle size in range of 0.5 mm-1.6 mm, and said sprinkle dosage form releases not more than 20% of quetiapine after two hours when measured in a United States Pharmacopeia (USP) type I dissolution apparatus, 200 rpm, at a temperature of 37° C.±0.5° C. in 900 mL of pH 4.80 citrate buffer media.

In another embodiment of the present invention, the multi-particulate dosage form releases about 30% to about 70% of quetiapine at eight hours, when measured in a United States Pharmacopeia (USP) type I dissolution apparatus, 200 rpm, at a temperature of 37° C.±0.5° C. in 1000 mL of pH 6.60 citrate buffer follow on media after $5^{th}$ hour of pH 4.80 citrate buffer media.

In one embodiment of the present invention, the multi-particulate dosage form releases not more than 10% of quetiapine after 2 hours, when measured in a United States Pharmacopeia (USP) type I dissolution apparatus, 200 rpm, at a temperature of 37° C.±0.5° C. in 1000 mL of pH 0.1 N HCl (40 mesh basket).

In another embodiment of the present invention, the multi-particulate dosage form releases not more than 30% of quetiapine when measured in a United States Pharmacopeia (USP) type I dissolution apparatus, 200 rpm, at a temperature of 37° C.±0.5° C. in 1000 mL of pH 6.60 phosphate buffer follow on media (after 2 hours dissolution in 0.1 NHCl) after $1^{st}$ hour of buffer stage (40 mesh basket).

In another embodiment of the present invention, the multi-particulate dosage form releases about 40% to about 70% of quetiapine when measured in a United States Pharmacopeia (USP) type I dissolution apparatus, 200 rpm, at a temperature of 37° C.±0.5° C. in 1000 mL of pH 6.60 phosphate buffer follow on media (after 2 hours dissolution in 0.1 NHCl) after $6^{th}$ hour of buffer stage (40 mesh basket).

In another embodiment of the present invention, the multi-particulate dosage form releases about 40% to about 70% of quetiapine when measured in a United States Pharmacopeia (USP) type I dissolution apparatus, 200 rpm, at a temperature of 37° C.±0.5° C. in 1000 mL of pH 6.60 phosphate buffer follow on media (after 2 hours dissolution in 0.1 NHCl) after $22^{nd}$ hour of buffer stage (40 mesh basket).

In one embodiment, the present invention provides a dosage form which is believed to be bio-equivalent to an extended release multi-particulate sprinkle dosage form comprising a plurality of discrete units, wherein each unit comprises: a drug core comprising quetiapine or a pharmaceutically acceptable salt thereof; an extended release coating and a delayed release coating surrounding the core, wherein the drug release from the multi-particulate dosage form is controlled by pH sensitive and pH neutral polymers in the coatings, wherein the AUC and Cmax is in the range 80-125%.

In another embodiment, the extended release multi-particulate sprinkle dosage form according to the present invention comprises a plurality of discrete units, wherein each unit comprises: a drug core comprising quetiapine or a pharmaceutically acceptable salt thereof; at least two coatings on drug core wherein one of the at least two coatings comprises a pH sensitive polymer, and wherein the release of the drug is controlled by a combination of the said at least two coatings, wherein administration of the sprinkle dosage form under fasting conditions provides AUC and Cmax values within the acceptable range of 80-125%.

In yet another embodiment, there is provided a pharmaceutical composition of quetiapine or a pharmaceutically acceptable salt thereof, wherein said composition is believed to be bioequivalent to an extended release multi-particulate sprinkle dosage form comprising a plurality of discrete units, wherein each unit comprises: a drug core comprising quetiapine or a pharmaceutically acceptable salt thereof; at least two coatings on the drug core wherein one of the at least two coatings comprises a pH sensitive polymer; and wherein the release of the drug is controlled by a combination of said at least two coatings, wherein administration of the sprinkle dosage form under fasting conditions provides AUC and Cmax values within the acceptable range of 80-125%.

In a further embodiment, the present invention provides an extended release multi-particulate sprinkle dosage form comprising a plurality of discrete units, wherein each unit comprises: a drug core comprising quetiapine or a pharmaceutically acceptable salt thereof; an extended release coating and a delayed release coating surrounding the core, wherein the drug release from the multi-particulate dosage form is controlled by pH sensitive and pH neutral polymers in the coatings, and the core is devoid of any release controlling polymer.

In one embodiment of the present invention, the multi-particulate composition is substantially free of an immediate release component.

In an embodiment of the present invention, the extended release coating comprises a combination of a pH neutral and a pH sensitive polymer.

The term "pH neutral polymer(s)" as used herein includes, but is not limited to, cellulose ethers such as ethyl cellulose; cellulose esters, polymethacrylic acid esters copolymers, e.g., Eudragit® NE 30 D, and Eudragit® NE 40 D aminoalkyl methacrylate copolymers, e.g., Eudragit® RL 100, Eudragit® RL PO, Eudragit® RS PO, and Eudragit® RS 100; polyvinyl acetate, copolymers of polyvinyl acetate and polyvinyl pyrrolidone, or a mixture thereof. Preferably, the pH neutral polymer is ethyl cellulose.

The term "pH sensitive polymer(s)" as used herein includes, but is not limited to, acrylic acid derivatives, e.g., methyl acrylate acrylic acid copolymer, methyl acrylate methacrylic acid copolymer, butyl acrylate styrene acrylic acid copolymer, methacrylic acid methyl methacrylate copolymer (e.g., Trade-names: Eudragit L 100 and Eudragit S, available from Rohm Pharma), methacrylic acid ethyl acrylate copolymer, e.g., Eudragit L 100-55, available from Rohm Pharma, methyl acrylate methacrylic acid octyl acrylate copolymer, cellulose derivatives e.g. cellulose acetate phthalate, cellulose acetate succinate, cellulose acetate maleate, cellulose acetate trimelliate, cellulose benzoate phthalate, cellulose propionate phthalate, methylcellulose phthalate, carboxymethylethylcellulose, ethylhydroxyethylcellulose phthalate, polyvinyl derivatives, e.g., polyvinyl alcohol phthalate, polyvinylacetal phthalate, polyvinyl butylate phthalate, polyvinylacetoacetal phthalate and maleic acid copolymers, or a mixture thereof.

In one embodiment, the present invention provides a high drug load sprinkle dosage form for nasogastric administration, wherein said dosage form comprises: quetiapine or its pharmaceutically acceptable salt in a dose range of 200-400 mg twice or thrice daily; which can be administered to psychiatric patients, or patients who are unconscious or are having swallowing difficulty. In a related embodiment of this aspect, the multi-particulate composition is sprinkled onto soft foods or edible material or liquids.

In yet another embodiment of the present invention, the multi-particulate composition is sprinkled onto soft foods, for example, applesauce, yogurt, cottage cheese, peaches purees, pears purees, lychee purees, apricots purees, grapes purees, strawberries purees, raspberries purees, or bananas purees at the time of administration. In a further embodiment of the present invention, the multi-particulate composition is sprinkled onto liquids, for example, cranberry juice, grape fruit juice, orange juice, pineapple juice, mango juice, apple juice, vegetable juice, tomatoes juice, water or milk at the time of administration. In a related embodiment of this invention, the multi-particulate composition when sprinkled onto soft foods or edible material or liquids are stable for at least about 15 minutes without affecting the stability of the extended release coating.

In another embodiment, the composition according to present invention is a multi-particulate dosage comprising a plurality of discrete units, where in each unit is separately coated thereby in case of accidental rupture of two or three pellets or granules there won't be any significant dose dumping.

In a further embodiment, the multi-particulate composition according to present invention also reduces the variability in bioavailability as the gastric emptying of the pellets or granules are not significantly impacted due to the size of pellets less than 2 mm.

In yet another embodiment of the present invention, the multi-particulate composition when sprinkled onto soft foods or edible material or liquids is stable to be administered immediately with food. In another embodiment of this aspect, the multi-particulate composition is suitable for administration to a patient via a feeding tube. In a further embodiment of this aspect, the feeding tube is a nasogastric (NG) tube or a gastric (G) tube.

In one embodiment of the present invention, the multi-particulate composition when dispersed in an aqueous media is stable when administered through a feeding tube after holding for at least 10 minutes.

In another embodiment, the present invention provides an extended release multi-particulate sprinkle dosage form comprising a plurality of discrete units, wherein the said multi-particulate sprinkle dosage form comprise coated discrete units having a particle size in range of 0.5 mm-1.6 mm, wherein the discrete units when exposed to water for 60 minutes in a syringe, and then passed through a 12 French nasogastric tube into a dissolution medium of 0.1N HCl, releases not more than 0.5% of quetiapine N-oxide impurity or not more than 0.5% of impurity C after 2 hours, when placed in 1000 mL of 0.1N HCl at 100 rpm in USP apparatus I.

In one embodiment, the extended release multi-particulate sprinkle dosage form according to present invention is stable for at least 6 months under storage conditions of 40° C./75% RH. In one embodiment according to present invention, the multi-particulate sprinkle dosage has controlled level of impurities after storage period of at least 6 months, wherein the dosage form contains not more than 0.5% of quetiapine N-oxide impurity (USP related compound H), contains not more than 0.5% of impurity C (USP related compound G), any unspecified degradation product not more than 0.5% and total impurities not more than 1% by weight of quetiapine.

In some embodiments, the extended release multi-particulate sprinkle dosage form according to present invention is stable for at least 6 months under storage conditions of 40° C./75% RH. In one embodiment according to present invention, the multi-particulate sprinkle dosage has controlled level of impurities after a storage period of at least 6 months, wherein the dosage form contains not more than 0.2% of quetiapine N-oxide impurity (USP related compound H), contains not more than 0.2% of impurity C (USP related compound G), any unspecified degradation product not more than 0.2% and total impurities not more than 0.6% by weight of quetiapine.

In another embodiment, the present invention provides an extended release multi-particulate sprinkle dosage form comprising a plurality of discrete units, wherein the said multi-particulate sprinkle dosage form comprise coated discrete units having a particle size in range of 0.5 mm-1.6 mm, wherein the discrete units when exposed to water for 60 minutes in a syringe, and then passed through a 12 French nasogastric tube into a dissolution medium of 0.1N HCl, releases not more than 0.2% of quetiapine N-oxide impurity or not more than 0.2% of impurity C after 2 hours, when placed in 1000 mL of 0.1N HCl at 100 rpm in USP apparatus I.

In another embodiment according to present invention, the multi-particulate sprinkle dosage form is stable for at least 6 months under storage condition of 40° C./75% RH, wherein the water content of the dosage form is not more than 8.0%, preferably not more than 5.0, more preferably not more than 3.5%, by weight of the composition.

In a preferred embodiment of the present invention, the multi-particulate composition comprising coated discrete units may be filled into a pouch or a sachet.

In yet another embodiment of the present invention, the weight of pellets or granules or spheroids filled in a sachet or a pouch may range from about 100 mg to about 200 mg for 50 mg strength of quetiapine; about 300 mg to about 600 mg for 150 mg; about 400 mg to about 800 mg for 200 mg strength of quetiapine; about 600 mg to about 1200 mg for 300 mg strength and about 800 mg to about 1600 mg for 400 mg strength of quetiapine.

The multi-particulate composition of present invention may further comprise pharmaceutically acceptable excipients, for example, binders, diluents, disintegrants, pore-formers, lubricants/glidants, surfactants, sweeteners, anti-tacking agents, opacifiers, anti-foaming agents, coloring agents, taste masking/flavoring agents, or a mixture thereof.

Examples of diluents that may be used in the present composition include, but are not limited to, microcrystalline cellulose, lactose, sorbitol, calcium dihydrogen phosphate dihydrate, calcium phosphate-dibasic, calcium phosphate-tribasic, calcium sulfate, silicified microcrystalline cellulose, mannitol, disaccharide sugars, starch, pregelatinized starch, or a mixture thereof.

Examples of binders that may be used in the present composition include, but are not limited to, corn starch, pregelatinized starch, microcrystalline cellulose, silicified microcrystalline cellulose, methyl cellulose, hydroxypropyl cellulose (HPC-L), methylcellulose, carboxymethyl cellulose sodium, guar gum, polyvinylpyrrolidone, or a mixture thereof.

Examples of plasticizers that may be used in the present composition include, but are not limited to, tributyl citrate, dibutyl sebacate, acetyl tributyl citrate, glyceryl monostearate, diethyl phthalate, castor oil, acetylated monoglycerides, diacetylated monoglycerides, cetyl alcohol, or a mixture thereof. The addition of plasticizer in the present invention helps in maintaining integrity of coating layer(s) while achieving a desired rate of release of quetiapine from multi-particulates.

Examples of lubricants and glidants that may be used in the present composition include, but are not limited to, colloidal anhydrous silica, stearic acid, magnesium stearate, glyceryl behenate, calcium stearate, sodium stearyl fumarate, stearic acid, talc, microcrystalline wax, yellow beeswax, white beeswax, or a mixture thereof.

Examples of the disintegrants that may be used in the present composition include, but are not limited to, crospovidone, sodium starch glycolate, sodium croscarmellose, guar gum, carboxymethylcellulose, low viscosity hydroxypropylcellulose, potassium polacrilin, or a mixture thereof.

Examples of surfactants that may be used in the present composition include, but are not limited to, sorbitan monostearate, polyoxyethylene sorbitan monostearate, e.g., Polysorbate 60 or Polysorbate 80, non-ethoxylated glyceryl monostearate, cetomacrogol, cetostearyl alcohol, sodium stearoyl lactylate, lecithin, or a mixture thereof.

Examples of sweeteners that may be used in the present composition include, but are not limited to, sucrose, sucralose, sorbitol, xylitol, dextrose, fructose, maltose, maltitol, acesulfame potassium, aspartame, saccharin, saccharin sodium, glucose, cyclamate, sodium cyclamate, or a mixture thereof.

Examples of opacifiers that may be used in the present composition include, but are not limited to, titanium dioxide, silicon dioxide, talc, calcium carbonate, behenic acid, or a mixture thereof.

Examples of anti-tacking agents that may be used in the present composition include, but are not limited to, talc, colloidal silicon dioxide, or a mixture thereof.

Examples of anti-foaming agents that may be used in the present composition include, but are not limited to, silicon based surfactants like polydimethylsiloxanes, e.g., simethicone; vegetable oils; waxes; hydrophobic silica; polyethylene glycol, or a mixture thereof.

Suitable solvents are selected from water, methyl alcohol, ethyl alcohol, isopropyl alcohol, n-butyl alcohol, acetone, acetonitrile, chloroform, methylene chloride, water, or a mixture thereof.

The coloring agents and flavoring agents of the present invention may be selected from any FDA approved suitable colors or flavors for oral use.

Coating may be carried out by using any conventional coating techniques known in the art, such as, spray coating in a conventional coating pan, fluidized bed processor, or dry powder coating, or a combination thereof.

The extended release multi-particulate composition of the present invention can be prepared by various methods including fluidized bed granulation, wet granulation, solvent evaporation, spray drying, or a combination thereof.

In yet another embodiment, the present invention provides a method for preparing a multi-particulate composition of quetiapine.

In one embodiment, the present invention provides use of a combination of at least two coatings for preparation of an extended release multi-particulate sprinkle dosage form of quetiapine, wherein out of the at least two coatings on a drug core at least one coating comprises a pH sensitive polymer, and wherein the release of the drug is controlled by a combination of the at least two coatings.

In another embodiment, the present invention provides an extended release multi-particulate sprinkle dosage form prepared by a process comprising mixing quetiapine or its pharmaceutically acceptable salt with suitable excipients and at least two coatings on a drug core wherein one of the at least two coatings comprises a pH sensitive polymer, and wherein the release of the drug is controlled by a combination of the at least two coatings.

In a further embodiment, the present invention provides a process of preparation of an extended-release multi-particulate composition comprising a plurality of discrete units comprising quetiapine or a pharmaceutical acceptable salt thereof, wherein the process comprises:
  i. mixing quetiapine or a pharmaceutical acceptable salt thereof with suitable pharmaceutical acceptable excipients in a dry mix followed by granulation using a suitable technique;
  ii. extruding the resultant from step i) followed by spheronization;
  iii. drying the resulting drug containing spheroids or granules or pellets from step ii);
  iv. drying and sifting the resultant from step iii);
  v. coating the drug containing core with a suitable pH neutral polymer;
  vi. coating the core further with a suitable pH sensitive polymer; and
  vii. lubricating the coated core followed by filling into a suitable sachet or pouch or capsule.

In a further embodiment, the present invention provides a process of preparation of an extended-release multi-particulate composition comprising a plurality of discrete units comprising quetiapine or a pharmaceutical acceptable salt thereof, wherein the process comprises:
  i. mixing quetiapine or a pharmaceutical acceptable salt thereof with suitable pharmaceutical acceptable excipients in a dry mix followed by granulation using a suitable technique;
  ii. extruding the resultant from step i) followed by spheronization;
  iii. drying the resulting drug containing spheroids or granules or pellets from step ii);
  iv. drying and sifting the resultant from step iii);
  v. coating the drug containing core with a suitable pH sensitive polymer;
  vi. coating the core further with a suitable pH neutral polymer, and
  vii. lubricating the coated core followed by filling into a suitable sachet or pouch or capsule.

In yet another related embodiment, the composition according to the present invention may further comprise a suitable non-functional coating.

In one embodiment, the present invention provides a method of treating various psychotic disorders. In an aspect, the present invention provides a method of treating schizophrenia. In another aspect, there is provided a method of treatment of maniac or mixed episodes associated with bipolar disorders. In a related aspect, the present invention also provides a monotherapy or an adjunct therapy with other known therapies for the treatment of manic or bipolar disorders. In a further aspect, the present invention provides an adjunctive treatment of a major depressive disorder.

In a further embodiment, the present invention provides a method of treating schizophrenia, major depression or bipolar disorder, said method comprising orally administering to a human in need thereof, the multi-particulate pharmaceutical composition of quetiapine according to the present invention.

In one embodiment, the present invention provides a use of an extended release multi-particulate composition comprising a plurality of discrete units of quetiapine or its pharmaceutically acceptable salt according to the present invention for treatment of schizophrenia, in management of acute manic or mixed episodes in patients with bipolar disorder, as a monotherapy or in combination with other drugs.

In one embodiment, the stable multi-particulate pharmaceutical composition according to the present invention is filled into a sachet or pouch or capsule with a controlled opening to avoid spillage of the contents of such packing. This is particularly helpful for geriatric patients or patients with poor locomotors control who have difficulty opening the sachet or pouch or capsule to empty the contents onto soft food or edible material or liquid. Particularly, the absence of fine powders in the multi-particulate pharmaceutical composition can avoid loss of the composition which may result from blowing of the fine powder while being emptied from the capsule or pouch onto the carrier solid or liquid food contents. Alternatively, the granules, pellets or spheroids can be administered from a device which dispenses them directly onto the soft food or edible material or liquid.

The following non-limiting examples illustrate the scope of the present disclosure without any limitation thereto. It is to be understood that the disclosed embodiments are merely exemplary of the invention, which can be embodied in various forms.

EXAMPLES

Example 1

Various batches of quetiapine compositions were prepared with different excipients to evaluate the impact of pH sensitive and pH neutral polymer:

| Ingredients | Example 1A | Example 1B |
|---|---|---|
| Quetiapine Fumarate | 230.270 | 230.270 |
| Tri sodium citrate anhydrous | 65.800 | 65.800 |
| Avicel PH101 | 41.930 | 41.930 |

-continued

| Ingredients | Example 1A | Example 1B |
|---|---|---|
| Pregelatinized starch (Lycatab PGS) | 20.000 | 20.000 |
| Colloidal anhydrous silica (Aerosil 200) | 2.000 | 2.000 |
| Core pellets | 360.00 | 360.00 |
| Opadry | 18.000 | 18.000 |
| Sub coated pellets wt. | 378.00 | 378.00 |
| Ethyl cellulose 20 cps | 6.910 | 6.910 |
| HPMC E5 | 8.446 | 8.446 |
| Dibutyl sebacate | 3.543 | 3.543 |
| ER coated pellets | 396.900 | 396.900 |
| DR/ER coating | DR | ER |
| Eudragit L 100 55 (Enteric) | 12.600 | — |
| Ethyl cellulose | — | 8.060 |
| HPMC E5 | 3.150 | 8.060 |
| Dibutyl sebacate | 2.580 | 3.720 |
| Talc | 1.550 | — |
| DR/ER coated pellets wt. | 416.78 | 416.74 |
| Talc | 1.220 | 1.260 |
| Total pellet weight | 418.00 | 418.00 |

TABLE 1

Bio results of Example 1A and 1B

| | | Fasting study results | | | | | |
|---|---|---|---|---|---|---|---|
| | | Example 1A | | | Example 1B | | |
| Based on comparison of Test/Reference | | ln Cmax (ng/mL) | ln AUC$_{0-t}$ (ng·hr/mL) | ln AUC$_{0-inf}$ (ng·hr/mL) | ln Cmax (ng/mL) | ln AUC$_{0-t}$ (ng·hr/mL) | ln AUC$_{0-inf}$ (ng·hr/mL) |
| Based on comparison of T/R | Ratio (%) (T/R) | 118.63 | 91.84 | 94.45 | 160.13 | 77.79 | 85.90 |
| | 90% Confidence Interval | 96.84-145.31 | 79.12-106.60 | 81.36-109.65 | 130.03-197.20 | 66.75-90.65 | 73.48-100.42 |

Observation: From the Table 1 fasting study, it was found that the samples from Example 1B showed risk of supra bioavailability with respect to Cmax as it did not have a pH sensitive polymer. Cmax was on the higher side 160% (target 100% in ratio Test/Reference) when a pH neutral polymer alone was used. When a combination of a pH sensitive and a pH neutral polymer was used in the multi-particulate system, the Cmax was within the acceptable range of 80-125%.

Example 2

Mixture of two different types of pellets: Pellet 1-70% w/w and Pellet 2-30% w/w, were filled in a single sachet or pouch.

Composition of Pellet 1 (70% w/w)

| Ingredients Drug Core Pellets | Quantity mg/unit dose |
|---|---|
| Quetiapine Fumarate eq. to quetiapine 200 mg | 230.270 |
| Microcrystalline cellulose (Avicel PH101) | 75.730 |
| Tri-Sodium Citrate dihydrate | 50.000 |
| Pregelatinized starch (Lycatab PGS) (Part A) | 7.000 |
| Pregelatinized starch (Lycatab PGS) (Part B) | 15.000 |
| Colloidal anhydrous silica | 2.000 |

-continued

| Ingredients Drug Core Pellets | Quantity mg/unit dose |
|---|---|
| Purified water | q.s. |
| Core pellet weight | 380 |
| DR Coating | |
| Eudragit L30D 55 (solids polymer) | 8.444 |
| PEG 400 | 1.267 |
| Talc | 1.689 |
| Purified water | q.s. |
| DR coated weight | 391.4 |
| ER Coating | |
| EC solids polymer (Aquacoat ARC I of II) | 63.865 |
| Guar gum (Aquacoat ARC II of II) | 9.124 |
| Dibutyl sebacate | 15.966 |
| Talc | 8.895 |
| Purified water | q.s. |
| ER coated pellet wt. | 489.25 |
| Top Coat | |
| Sodium Alginate CR8133 | 39.453 |
| PEG 6000 | 5.793 |
| Talc | 52.604 |
| Purified water | q.s. |
| Total pellet weight per unit | 587.1 |

Composition of Pellet 2 (30% w/w)

| Ingredients Drug Core Pellets | Quantity mg/unit dose |
|---|---|
| Quetiapine Fumarate eq. to quetiapine 200 mg | 230.270 |
| Microcrystalline cellulose (Avicel PH101) | 75.730 |
| Tri-Sodium Citrate dihydrate | 50.000 |
| Pregelatinized starch (Lycatab PGS) (Part A) | 7.000 |
| Pregelatinized starch (Lycatab PGS) (Part B) | 15.000 |
| Colloidal anhydrous silica | 2.000 |
| Purified water | q.s. |
| Core pellet weight | 380 |
| DR Coat | |
| Hypromellose Acetate Succinate HF | 95.00 |
| Talc | 19.00 |
| Isopropyl alcohol | q.s. |
| Purified water | q.s. |
| DR coated pellet wt. | 494.00 |
| TopCoat | |
| Sodium Alginate CR8133 | 39.84 |
| PEG 6000 | 5.85 |
| Talc | 53.12 |
| Total weight | 592.80 |

TABLE 2

Bio results of Example 2 in fasting and food effect conditions:

| | In Cmax (ng/mL) | In $AUC_{0-t}$ (ng · h/mL) | In $AUC_{0-inf}$ (ng · h/mL) |
|---|---|---|---|
| Quetiapine: Fasting Equivalence | | | |
| Ratio of Test Reference (90% CI) | 124.83 | 87.95 | 86.81 |
| Quetiapine: Food Effect | | | |
| Ratio of Test & Reference (90% CI) | 110.79 | 108.05 | 107.97 |

Observation: From the Table 2 Bio-study it was found that the presence of food showed little or no food effect.

Example 3

200 mg equivalent of quetiapine formulation were prepared as per the composition shown below:

| S. No | Ingredients | A | B | C | D | E | F | G | H |
|---|---|---|---|---|---|---|---|---|---|
| | | % w/w per Sachet | | | | | | | |
| | Drug core | | | | | | | | |
| 1 | Quetiapine fumarate | 230.270 | 230.265 | 230.265 | 230.265 | 230.265 | 230.265 | 230.265 | 230.265 |
| 2 | Microcrystalline cellulose (PH101) | 75.730 | 75.735 | 75.735 | 75.735 | 75.735 | 75.735 | 75.735 | 75.735 |
| 3 | Tri Sodium Citrate dihydrate | 50.000 | 50.000 | 50.000 | 50.000 | 50.000 | 50.000 | 50.000 | 30.000 |
| 4 | Pregelatinized starch | 22.000 | 22.000 | 22.000 | 22.000 | 22.000 | 22.000 | 22.000 | 22.000 |
| 6 | Colloidal anhydrous silica | 2.000 | 2.000 | 2.000 | 2.000 | 2.000 | 2.000 | 2.000 | 2.000 |
| 7 | Purified water | q.s. | q.s. | q.s. | q.s. | q.s. | q.s. | q.s. | q.s. |
| | ER Coating | | | | | | | | |
| 8 | Ethyl cellulose dispersion (Solid) | 62.005 | 39.683 | 43.084 | 39.683 | 49.603 | 62.004 | 49.603 | 39.683 |
| 9 | Guar gum | 8.858 | 5.669 | 2.241 | 5.669 | 7.086 | 8.858 | 7.086 | 5.669 |
| 10 | Dibutyl sebacate | 15.501 | 9.921 | 9.921 | 9.921 | 12.401 | 15.501 | 12.401 | 9.921 |
| 11 | Talc | 8.636 | 5.527 | 5.527 | 5.527 | 6.910 | 8.637 | 6.910 | 5.527 |
| 12 | Purified water | q.s. | q.s. | q.s. | q.s. | q.s. | q.s. | q.s. | q.s. |

-continued

| S. No | Ingredients | % w/w per Sachet | | | | | | | |
|---|---|---|---|---|---|---|---|---|---|
| | | A | B | C | D | E | F | G | H |
| DR coating | | | | | | | | | |
| 13 | Eudragit L30D 55 (solid) | 70.370 | 65.304 | 65.304 | 70.528 | 54.044 | 39.970 | 67.556 | 65.304 |
| 14 | Talc | 14.074 | 13.061 | 13.061 | 8.816 | 8.107 | 5.996 | 10.133 | 13.061 |
| 15 | PEG 400 | 10.556 | 9.795 | 9.795 | 8.816 | 10.809 | 7.994 | 13.511 | 9.795 |
| 16 | Purified water | q.s. | q.s. | q.s. | q.s. | q.s. | q.s. | q.s. | q.s. |
| Top Coat | | | | | | | | | |
| 17 | HPMC 6 CPS | 19.136 | — | — | — | — | — | — | — |
| 18 | Carbopol 971 P | 1.222 | — | — | — | — | — | — | — |
| 19 | Talc | 8.144 | — | — | — | — | — | — | — |
| 20 | Isopropyl alcohol | q.s. | — | — | — | — | — | — | — |
| 21 | Purified water | q.s. | — | — | — | — | — | — | — |
| Lubrication | | | | | | | | | |
| 22 | Talc | — | 5.290 | 5.290 | 5.290 | 5.290 | 5.290 | 5.290 | 5.290 |
| | Final Weight | 598.502 | 534.250 | 534.250 | 534.250 | 534.250 | 534.250 | 552.672 | 514.250 |

Manufacturing Process Example 3A

1. Quetiapine, microcrystalline cellulose, part of pregelatinised starch and colloidal silicon dioxide were mixed in a dry mix followed by the addition of sodium citrate and remaining part of pregelatinised starch in purified water;
2. The resulting mixture from step 1) was then granulated in a rapid mixture granulator,
3. The resulting mass from step 2) was extruded and spheronized to form particulates as spheroids/pellets/granules which were subjected to drying and sifting;
4. A dispersion of ethyl cellulose was prepared, guar gum and dibutyl sebacate and purified water added to it;
5. Then the step 3) sifted particulates were coated with the dispersion of step 4) to obtain extended release coated cores.
6. A delayed release coat of Eudragit L 30 D 55, polyethylene glycol, talc and purified water was coated onto the step 5) extended release coated cores.
7. HPMC and Carbopol were dissolved in isopropyl alcohol and water followed by coating the delayed release coated particles of step 6) followed by lubrication with talc and filling into sachet.

Manufacturing Process Example 3(B-H)

1. Quetiapine, microcrystalline cellulose, part of pregelatinised starch and colloidal silicon dioxide were mixed in dry mix followed by addition of sodium citrate and remaining part of pregelatinised starch in purified water;
2. The resulting mixture from step 1) was then granulated in a rapid mixture granulator,
3. The resulting mass from step 2) was extruded and spheronized to form spheroids/pellets which were subjected to drying and sifting;
4. A dispersion of ethyl cellulose was prepared, guar gum and dibutyl sebacate and purified water added to it;
5. Then the step 3) sifted spheroids/pellets were coated with the dispersion of step 4) to obtain extended release coated cores.
6. A delayed release coat of Eudragit L 30 D 55, polyethylene glycol, talc and purified water was coated onto the step 5) extended release coated cores.
7. The resulting delayed release coated core particles were then lubricated with talc and filled into sachet.

TABLE 3

Bio results of Example 3B in fasting and food effect study conditions:

| Ratio of Test and Reference | In $C_{max}$ (ng/mL) | In $AUC_{0-t}$ (ng · hr/mL) | In $AUC_{0-inf}$ (ng · hr/mL) |
|---|---|---|---|
| Fasting Condition | | | |
| Ratio (%) (T/R) | 106.89 | 94.79 | 95.23 |
| 90% Confidence Interval | 91.50-124.86 | 87.92-102.19 | 88.48-102.49 |
| Intra-Subject CV (%) | 27.07 | 12.92 | 12.63 |
| Food Effect Study | | | |
| Ratio(%)(T/R) | 111.48 | 112.17 | 110.95 |
| 90% Confidence Interval | 96.95-128.20 | 103.85-121.15 | 102.89-119.65 |
| Intra-Subject CV (%) | 24.25 | 13.24 | 12.96 |

Observation: From Table 3, fasting data and the food effect data shows that food has no effect on the drug release from the multi-particulate composition according to the present invention and the Cmax was within the acceptable range of 80-125%.

Example 4

50 mg, 200 mg and 400 mg equivalent of quetiapine formulations were prepared as per the compositions shown below:

|  | % w/w per Sachet | | | | | | | | |
|---|---|---|---|---|---|---|---|---|---|
| S. No | 50 mg Strength | | | 200 mg Strength | | | 400 mg Strength | | |
| Ingredients | A | B | C | D | E | F | G | H | I |
| *Drug core* | | | | | | | | | |
| Quetiapine fumarate equivalent to Quetiapine base | 57.571 | 57.556 | 57.566 | 230.270 | 230.265 | 230.265 | 460.539 | 460.530 | 460.389 |
| Microcrystalline cellulose | 17.491 | 19.592 | 18.934 | 78.132 | 75.735 | 81.242 | 148.91 | 151.47 | 153.35 |
| Sodium Citrate (tri sodium citrate dihydrate) | 13.5 | 11.8 | 12.500 | 48.0 | 50.0 | 53.0 | 91.500 | 100 | 104 |
| Pregelatinized starch | 6.3 | 4.8 | 5.500 | 24 | 22 | 18 | 48 | 44 | 39 |
| Colloidal Silicon dioxide | 1 | 0.7 | 0.5 | 5 | 2 | 4 | 8 | 4 | 6 |
| Purified water* | q.s. | q.s. | q.s. | q.s. | q.s. | q.s. | q.s. | q.s. | q.s. |
| Weight of Core | 95.847 | 94.448 | 95.0 | 385.402 | 380.0 | 386.507 | 756.949 | 760.0 | 762.739 |
| *ER Coating* | | | | | | | | | |
| Ethyl cellulose aq. dispersion (Solid)# | 10.227 | 10.836 | 9.921 | 38.643 | 39.683 | 41.503 | 85.554 | 79.366 | 74.756 |
| Guar gum | 1.65 | 1.81 | 1.417 | 5.137 | 5.669 | 4.328 | 12.160 | 11.338 | 15.312 |
| Dibutyl sebacate | 2.92 | 3.17 | 2.48 | 8.789 | 9.921 | 7.786 | 17.435 | 19.842 | 16.811 |
| Talc | 1.41 | 1.16 | 1.382 | 5.231 | 5.527 | 3.245 | 9.853 | 11.054 | 12.348 |
| Purified water* | q.s. | q.s. | q.s. | q.s. | q.s. | q.s. | q.s. | q.s. | q.s. |
| Weight of extended release pellets | 112.054 | 111.424 | 110.2 | 443.202 | 440.8 | 443.369 | 881.951 | 881.6 | 881.966 |
| *DR coating* | | | | | | | | | |
| Methacrylic acid copolymer Dispersion USNF equivalent to dry polymer^ | 17.505 | 15.807 | 16.326 | 64.461 | 65.304 | 62.952 | 134.463 | 130.608 | 135.392 |
| Polyethylene glycol 400 | 3.141 | 2.865 | 2.449 | 8.819 | 9.795 | 11.138 | 18.651 | 19.590 | 21.262 |
| Talc | 3.86 | 2.953 | 3.265 | 14.561 | 13.061 | 12.465 | 23.412 | 26.122 | 19.819 |
| Purified water* | q.s. | q.s. | q.s. | q.s. | q.s. | q.s. | q.s. | q.s. | q.s. |
| Weight of delayed release pellets | 136.56 | 133.049 | 145.676 | 531.043 | 528.96 | 529.924 | 1058.477 | 1057.92 | 1058.433 |
| *Lubrication* | | | | | | | | | |
| Talc | 1.1 | 0.81 | 0.960 | 5.421 | 3.840 | 4.876 | 8.551 | 7.680 | 11.132 |
| Weight of lubricated pellets | 137.66 | 133.859 | 133.200 | 536.464 | 532.800 | 534.8 | 1067.028 | 1065.600 | 1069.565 |

*Evaporates during processing;
30% of dispersion taken in solid form;
^30% of dispersion taken as dry polymer;
aq. Aqueous Stability Data: The samples of Example 4 were kept for stability studies for 1, 3 and 6 months, respectively. The stability analysis was done using an assay method for determining the content of drug in the stored stability samples of Example 4. The stability analysis was also done by performing dissolution studies at 0.1N HCl medial 1000 ml for 2 hour, followed by pH 6.60 phosphate buffer media (1000 ml); in USP-I with (40 mesh basket) at 200 RPM. The details of stability study results are provided in below Table 4 and Table 5:

TABLE 4

Stability study data of 50 mg and 200 mg strength samples:

| | | | 50 mg | | | | 200 mg | | | |
| | | | 40° C./75% RH | | | | 40° C./75% RH | | | |
| Test | Strength | Stage -> Spec. | Initial | 1 M | 3 M | 6 M | Initial | 1 M | 3 M | 6 M |
|---|---|---|---|---|---|---|---|---|---|---|
| Assay | | 90-110% | 98.6 | 98.8 | 104.8 | 104.6 | 98.7 | 102.3 | 101.1 | 99.4 |
| Dissolution | | | | | | | | | | |
| Acid stage - 2 hr | | NMT 10% | 0 | 1 | 0 | 0 | 0 | 0 | 1 | 0 |
| Buffer Stage - 1 hr | | NMT 30% | 19 | 20 | 16 | 18 | 18 | 18 | 21 | 19 |
| Buffer stage - 6 hr | | 40%-70% | 59 | 56 | 55 | 50 | 53 | 54 | 58 | 54 |
| Buffer Stage - 22 hr | | NLT 80% | 99 | 96 | 94 | 95 | 93 | 97 | 101 | 92 |

TABLE 4-continued

Stability study data of 50 mg and 200 mg strength samples:

| Strength | | 50 mg 40° C./75% RH | | | | 200 mg 40° C./75% RH | | | |
|---|---|---|---|---|---|---|---|---|---|
| Test | Stage -> Spec. | Initial | 1 M | 3 M | 6 M | Initial | 1 M | 3 M | 6 M |
| Related Substance | | | | | | | | | |
| Quetiapine N Oxide (USP Related compound H) | NMT 0.2% | 0.03 | 0.04 | 0.05 | 0.06 | 0.03 | 0.04 | 0.05 | 0.05 |
| Impurity C (USP Related compound G) | NMT 0.2% | BLQ | BLQ | 0.01 | 0.01 | BLQ | BLQ | 0.01 | 0.01 |
| Any individual unspecified degradation product | NMT 0.2% | 0.01 | 0.04 | 0.01 | 0.01 | BLQ | 0.04 | 0.01 | 0.01 |
| Total impurities | NMT 0.6% | 0.03 | 0.04 | 0.10 | 0.1 | 0.03 | 0.04 | 0.09 | 0.11 |
| Water by KF | NMT 8.0% | 1.87 | 2.01 | 2.07 | 2.29 | 1.75 | 1.95 | 1.84 | 2.21 |

Note:
BLQ—below limit of quantification;
NMT—Not More Than;
NLT—Not Less Than;
USP—United States Pharmacopoeia;
HCl—Hydrochloric Acid;

TABLE 5

Stability study data of 400 mg strength samples:

| Strength | | 400 mg 40° C./75% RH | | | |
|---|---|---|---|---|---|
| Test | Spec. | Initial | 1 M | 3 M | 6 M |
| Assay | 90-110% | 101.1 | 98.9 | 98.6 | 98.1 |
| Dissolution: | | | | | |
| Acid stage - 2 hr | NMT 10% | 0 | 0 | 0 | 0 |
| Buffer Stage - 1 hr | NMT 30% | 18 | 15 | 11 | 21 |
| Buffer stage - 6 hr | 40%-70% | 51 | 48 | 47 | 51 |
| Buffer Stage - 22 hr | NLT 80% | 88 | 89 | 92 | 94 |
| Related Substance: | | | | | |
| Quetiapine N Oxide (USP Related compound H) | NMT 0.2% | 0.03 | 0.04 | 0.05 | 0.06 |
| Impurity C (USP Related compound G) | NMT 0.2% | BLQ | BLQ | 0.01 | 0.004 |
| Any individual unspecified degradation product | NMT 0.2% | BLQ | 0.04 | 0.01 | 0.02 |
| Total impurities | NMT 0.6% | 0.03 | 0.08 | 0.12 | 0.14 |
| Water byKF | NMT 8.0% | 1.85 | 1.79 | 1.74 | 2.99 |

Note:
BLQ-below limit of quantification;
NMT—Not More Than;
NLT—Not Less Than;
USP—United States Pharmacopoeia;
HCl—Hydrochloric Acid;
Since all five strengths (50 mg, 150 mg, 200 mg, 300 mg and 400 mg) are dose proportional, stability of data of intermediate strengths (150 mg and 300 mg) has not been generated.

Observation: From Table 4 and Table 5, stability data for assay and dissolution shows that:
the assay of the drug was within the acceptable specification limits of 90.0%-110.0%,
the dissolution values of the stability batches were also within the acceptable limit of NMT 10% in acid stage and NLT 80% at end of Buffer stage, and
the water content was also NMT 8.0%.
The samples of all the strengths used in the stability studies were found to be stable for at least for 6 months.
Abbreviations:
DR: Delayed Release.
ER: Extended Release.
T/R Ratio: Test/Reference Ratio
Intra-subject CV: Intra-subject Coefficient of Variation
AUC: Area under the plasma concentration-time curve
$C_{max}$: Maximum plasma concentration.
NLT: Not less than.
NMT: Not more than.
BLQ—below limit of quantification.
USP—United States Pharmacopoeia.

The invention claimed is:
1. An extended release multi-particulate sprinkle dosage form comprising a plurality of discrete units, wherein each unit comprises:

a) a drug core comprising an active pharmaceutical ingredient and pharmaceutically acceptable excipients, wherein the active pharmaceutical ingredient consists of quetiapine or a pharmaceutically acceptable salt thereof;
b) at least two coatings on the drug core and a pore former wherein a first of the at least two coatings is an extended release coating comprising a pH neutral polymer and a second of the at least two coatings comprises a pH sensitive polymer;

wherein the pore former is in the extended release coating and the ratio of PH neutral polymer and pore former in the extended release coating is 80:20 to 95:5, and wherein the release of the drug is controlled by a combination of said at least two coatings, wherein said dosage form with high fat meals results in not more than a 35% change in Cmax or AUC when compared to a similar dosing under fasting condition.

2. The extended release multi-particulate sprinkle dosage form according to claim 1, wherein the second of the at least two coatings is a delayed release coating.

3. The extended release multi-particulate sprinkle dosage form according to claim 2, wherein the extended release coating comprises a pH neutral polymer in an amount of about 50% to about 80% based on the weight of the extended release coating.

4. The extended release multi-particulate sprinkle dosage form according to claim 2, wherein the delayed-release coating comprises a pH sensitive polymer in an amount of about 55% to about 95% based on the weight of the delayed-release coating.

5. The extended release multi-particulate sprinkle dosage form according to claim 1 wherein the drug core is devoid of any release controlling polymer.

6. The extended release multi-particulate sprinkle dosage form according to claim 1, wherein the coating further comprises an optional non-functional coating.

7. The extended release multi-particulate sprinkle dosage form according to claim 1, wherein said composition further comprises pharmaceutically acceptable excipients selected from a diluent, a binder, a disintegrant, a pore-former, a lubricant, a glidant, a surfactant, a sweetener, an anti-tacking agent, an opacifier, an anti-foaming agent, a coloring agent, a flavoring agent, or a mixture thereof.

8. The extended release multi-particulate sprinkle dosage form according to claim 1, wherein the drug release from the multi-particulate dosage form is controlled with a combination of at least one pH neutral polymer in a pH neutral coating and at least one pH sensitive polymer in a pH sensitive coating.

9. The extended release multi-particulate sprinkle dosage form according claim 1, wherein the dosage form is in the form of a sachet, pouch or capsule.

10. The extended release multi-particulate sprinkle dosage form according to claim 1, wherein at least one of the discrete units is a form selected from a pellet, a bead, a particle, a granule or a mini-tablet.

11. The extended release multi-particulate sprinkle dosage form according to claim 1, wherein the pH neutral polymer is a water-insoluble polymer.

12. The extended release multi-particulate sprinkle dosage form according to claim 1, wherein the dosage form the ratio of the pH neutral polymer and the pore former is not more than 10% by weight of the extended release coating.

13. The extended release multi-particulate sprinkle dosage form according to claim 1, wherein D50 of at least one of said discrete units is in a range of about 0.7 to 1.3 mm or particle size of the discrete units is less than about 1.6 mm.

14. The extended release multi-particulate sprinkle dosage form according to claim 1, wherein the administration of the sprinkle dosage form under fasting conditions provides a Cmax in range of about 180 ng/mL to about 450 ng/mL and/or a mean $AUC_{0-inf}$ in the range of 4000 hr.ng/mL to 4800 hr.ng/mL.

15. The extended release multi-particulate sprinkle dosage form according to claim 1, wherein the administration of the sprinkle dosage form under fed conditions provides a Cmax in range of about 250 ng/mL to about 650 ng/mL and/or a mean $AUC_{0-inf}$ in the range of 4300 hr.ng/mL to 6300 hr.ng/mL.

16. The extended release multi-particulate sprinkle dosage form according to claim 1 wherein, a higher amount of quetiapine in a dose range of 50-400 mg can be administered as a sprinkle dosage form for nasogastric administration, wherein the dosage form can be administered to a patient suffering from a psychiatric disorder selected from schizophrenia, bipolar disorder, mania, depression where patients are unconscious or having swallowing difficulty.

17. A method for treating a patient suffering from a psychotic disorders selected from schizophrenia, bipolar disorder, mania, or depression, or as an adjunctive therapy with an antidepressant, by administering a therapeutically effective amount of a multi-particulate quetiapine sprinkle dosage form according to claim 1.

18. An extended release multi-particulate sprinkle dosage form prepared by a process comprising:
 mixing quetiapine or its pharmaceutically acceptable salt with suitable excipients and at least two coatings on a drug core wherein one of the at least two coatings comprises a pH sensitive polymer; and
 wherein the release of the drug is controlled by a combination of the at least two coatings.

19. The method of claim 18, wherein said process comprises:
 i. mixing quetiapine or a pharmaceutical acceptable salt thereof with suitable pharmaceutical acceptable excipients in a dry mix followed by granulation using a suitable technique;
 ii. extruding the resultant from step i above followed by spheronization;
 iii. drying the resulting drug containing spheroids;
 iv. sifting the resultant from step iii above;
 v. coating the drug containing core with suitable coatings; and
 vi. lubricating the coated core followed by filling into a suitable sachet or pouch or capsule.

20. The method of claim 18,
 wherein said excipient is selected from a diluent, a binder, a disintegrant, a pore-former, a plasticizer, a lubricant, a glidant, a surfactant, a sweetener, an anti-tacking agent, an opacifier, an anti-foaming agent, a coloring agent, a flavoring agent or a mixture thereof.

* * * * *